(12) United States Patent
Beato et al.

(10) Patent No.: US 10,941,093 B2
(45) Date of Patent: Mar. 9, 2021

(54) PROCESS FOR OXIDATION OF A LOWER ALKANE AT LOW TEMPERATURES IN AMMONIA-CONTAINING GAS MIXTURES

(71) Applicant: HALDOR TOPSØE A/S, Kgs. Lyngby (DK)

(72) Inventors: Pablo Beato, København S (DK); Ton V. W. Janssens, Bagsværd (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/619,270

(22) PCT Filed: Jun. 7, 2018

(86) PCT No.: PCT/EP2018/064954
§ 371 (c)(1),
(2) Date: Dec. 4, 2019

(87) PCT Pub. No.: WO2018/234044
PCT Pub. Date: Dec. 27, 2018

(65) Prior Publication Data
US 2020/0095182 A1    Mar. 26, 2020

(30) Foreign Application Priority Data
Jun. 23, 2017    (DK) .......................... PA 2017 00374

(51) Int. Cl.
| C07C 29/48 | (2006.01) |
| B01J 23/72 | (2006.01) |
| B01J 29/76 | (2006.01) |
| C07C 29/50 | (2006.01) |
| B01J 29/85 | (2006.01) |

(52) U.S. Cl.
CPC .............. *C07C 29/48* (2013.01); *B01J 23/72* (2013.01); *B01J 29/763* (2013.01); *C07C 29/50* (2013.01); *B01J 29/85* (2013.01)

(58) Field of Classification Search
CPC ......... C07C 28/48; C07C 28/50; C07C 29/48; C07C 29/50; B01J 23/72; B01J 29/763; B01J 29/85
See application file for complete search history.

(56) References Cited

U.S. PATENT DOCUMENTS

| 3,965,185 A | 6/1976 | Young |
| 2001/0044557 A1 | 11/2001 | Bhasin et al. |
| 2009/0050535 A1 | 2/2009 | Evans |
| 2011/0152546 A1 | 6/2011 | Senkan et al. |
| 2017/0000213 A1 | 1/2017 | Mason et al. |

FOREIGN PATENT DOCUMENTS

| CN | 101985016 A | 3/2011 |
| EP | 2980082 A1 | 2/2016 |
| EP | 3090997 A1 | 11/2016 |
| GB | 1373489 A | 11/1974 |
| JP | S53012803 A | 2/1978 |
| WO | 9505896 A1 | 3/1995 |
| WO | 2004078737 A1 | 9/2004 |
| WO | 2011046621 A1 | 4/2011 |
| WO | 2012009052 A1 | 1/2012 |
| WO | 2012141942 A1 | 10/2012 |
| WO | 2015154827 A1 | 10/2015 |
| WO | 2015154828 A1 | 10/2015 |
| WO | 2015154829 A1 | 10/2015 |
| WO | 2016177924 A1 | 11/2016 |
| WO | 2017083338 A1 | 5/2017 |
| WO | 2017083773 A1 | 5/2017 |
| WO | WO 2017/083773 | * 5/2017 ............. C07C 29/50 |

OTHER PUBLICATIONS

Shwan, S., et al., Solid-state ion-exchange of copper into zeolites facilitated by ammonia at low temperature, ACS Catalysis, vol. 5, pp. 16-19 (Year: 2015).*
Sheppard, T., et al., A low temperature, isothermal gas-phase system vor conversin of methane to methanol voer Cu-ZSM-5, Chem . Comm., vol. 50, pp. 11053-11055 (Year: 2014).*
Wulfers, M.J., et al., Conversin of methane to methanol on copper-containing small-pore zeolites and zeotypes, Chem. Comm., vol. 51, pp. 4447-4450 (Year: 2015).*
Groothaert, M. H. et al., "Selective Oxidation of Methane by the Bis(í-oxo)dicopper Core Stabilized on ZSM-5 and Mordenite Zeolites" J. Am. Chem. Soc. vol. 127, No. 5, pp. 1394-1395, Jan. 15, 2005).
Smeets, P. J. et al., "Cu based zeolites: A UV-vis study of the active site in the selective methane oxidation at low temperatures" Elsevier, Catal. Today 110, pp. 303-309, (2005).
Alayon, E. M. C. et al., "Reaction Conditions of Methane-to-Methanol Conversion Affect the Structure of Active Copper Sites" ACS Catalysis, vol. 4, No. 16, pp. 16-22, (2014).
Le, H. et al., "Solid-State Ion-Exchanged Cu/Mordenite Catalysts for the Direct Conversion of Methane to Methanol" ACS Catal., vol. 7, pp. 1403-1412, (2017).
Markovits, M. A. C. et al., "Effect of Location and Distribution of Al Sites in ZSM-5 on the Formation of Cu-Oxo Clusters Active for Direct Conversion of Methane to Methanol" Top. Catal., vol. 59, pp. 1554-1563, (2016).
Sushkevich, V. L. et al., "Selective anaerobic oxidation of methane enables direct synthesis of methanol" Science 356, pp. 523-527, May 5, 2017.

(Continued)

*Primary Examiner* — Yate' K Cutliff

(74) *Attorney, Agent, or Firm* — Buchanan Ingersoll & Rooney P.C.

(57) ABSTRACT

In a process for the oxidation of a lower alkane, such as methane, over a catalyst containing Cu and one or more zeolite or zeotype materials, the oxidation is conducted in the presence of ammonia in the feed gas at a process temperature below 350° C. The oxidation can be performed in a continuous process.

15 Claims, No Drawings

(56) References Cited

OTHER PUBLICATIONS

Gao, F. et al. "Understanding ammonia selective catalytic reduction kinetics over Cu/SSZ-13 from motion of the Cu ions" J. Catal. vol. 319, pp. 1-14, (2014).
Janssens, T.V. W. et al., "A Consistent Reaction Scheme for the Selective Catalytic Reduction of Nitrogen Oxides with Ammonia" ACS Catal., vol. 5, pp. 2832-2845, (2015).
Paolucci, C. et al., "Catalysis in a Cage: Condition-Dependent Speciation and Dynamics of Exchanged Cu Cations in SSZ-13 Zeolites" J. Am. Chem. Soc., vol. 138, pp. 6028-6048, (2016).
Shwan, S. et al., "Solid-State Ion-Exchange of Copper into Zeolites Facilitated by Ammonia at Low Temperature" ACS Catal. vol. 5, pp. 16-19, (2015).
International Search Report (PCT/ISA/210) and Written Opinion (PCT/ISA/237) dated Sep. 11, 2018, by the European Patent Office as the International Searching Authority for International Application No. PCT/EP2018/064954.
Search Report dated Oct. 23, 2017, by the Danish Patent Office for Application No. PA 2017 00374.

\* cited by examiner

PROCESS FOR OXIDATION OF A LOWER ALKANE AT LOW TEMPERATURES IN AMMONIA-CONTAINING GAS MIXTURES

The present invention relates to a process for oxidation of a lower alkane, such as methane, in ammonia-containing gas mixtures and catalysts for use in the process. The invention is based on the finding that oxygen can be activated by mobile Cu-ammonia complexes formed inside the cavities of a zeolite. The term "lower alkane" refers to an alkane containing from 1 to 5 carbon atoms in the molecule.

Methane is the main component in natural gas and an important resource for chemicals. The current technology for the production of hydrogen and CO is by steam reforming of methane: $CH_4+H_2O<->3H_2+CO$. This is an endothermic reaction that is conducted at temperatures 600->1000° C. with a high energy cost. For this reason, it is desirable to find alternative ways to exploit methane as a raw material for production of valuable chemicals. The challenge is that activation of methane with oxygen is difficult and often requires a high energy consumption.

Recently, it has been found that Cu-zeolites are able to oxidize methane directly to methanol at around 200° C. (M. H. Groothaert et al., J. Am. Chem. Soc. 127, 1394 (2005); P. J. Smeets et al., Catal. Today 110, 303 (2005), E. M. C. Alayon et al., ACS Catal. 4, 16 (2014); Le, H. et al., ACS Catal. 7, 1403-1412 (2017); Markovits, M. A. C. et al., Top. Catal. 59, 1554-1563 (2016)), which are very mild conditions for the activation of methane. However, the procedure for the conversion to methanol requires an activation of the Cu-zeolite which comprises exposure of the Cu-zeolite to oxygen at temperatures above 400° C. to activate the oxygen. The current interpretation of this partial oxidation of methane to methanol is that the oxidation reaction requires the formation of dimeric Cu—O species, such as Cu—O—Cu, Cu—O—O—Cu, or Cu—O$_2$—Cu, where the actual oxidation of methane then takes place.

A process for the direct selective conversion of methane to methanol at a temperature below 300° C., using an oxygen-activated Cu-based zeolite, is described in WO 2011/046621 A. While the methane-to-methanol conversion temperature is fairly low, the Cu-zeolite has to be pre-treated first, resulting in a cyclic process. Activation is done by heating the catalyst to about 350-750° C. in an oxidizing gaseous environment. For the actual conversion, the gaseous environment needs to be changed and cooled to the desired conversion temperature.

EP 3 090 997 A1 discloses a process for an isothermal conversion of methane to methanol at temperatures below 280° C., using an activated material. The process gives good yields of methanol, however this process is a discontinuous cyclic process and requires reactivation of the material after each cycle. In addition, high yields are only obtained if a high pressure of methane is applied.

CN 101985016 A discloses a catalyst preparation method and application thereof for low temperature oxidation of methane to methanol. Different amounts of air and methane are reacted batch-wise (i.e. non-continuous) in an autoclave at temperatures from 60 to 150° C. and pressures ranging from 0.5 to 2.0 MPa.

Very recently, Sushkevich et al., Science 356, 523-527 (2017), describe a discontinuous process where the oxidant is water instead of oxygen. One advantage of this anaerobic process is the higher selectivity towards methanol and the formation of $H_2$ as a valuable by-product.

Cu-zeolites are also well known catalysts for the selective catalytic reduction of NOx by ammonia ($NH_3$-SCR), which is the basis for the current technology for reduction of NOx emissions from diesel engines and power plants. The $NH_3$-SCR reaction proceeds according to the equation:

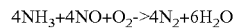

$4NH_3+4NO+O_2->4N_2+6H_2O$

According to this reaction equation, the $NH_3$-SCR reaction also requires an activation of oxygen. On Cu-zeolites, the $NH_3$-SCR reaction proceeds already around 200-250° C. (Gao, F. et al. J. Catal. 319, 1-14 (2014); Janssens, T. V. W. et al., ACS Catal. 5, 2832-2845 (2015); Paolucci, C. et al. J. Am. Chem. Soc. 138, 6028-6048 (2016)). As can be inferred from the reaction equation, this reaction also requires an activation of oxygen on the Cu-zeolites, which implies that oxygen activation takes place at around 200-250° C. in $NH_3$-SCR.

In $NH_3$-SCR, it has been found that the interaction between $NH_3$ and Cu plays a special role. Cu forms stable complexes with ammonia, such as $Cu(NH_3)_4^{2+}$ and $Cu(NH_3)_2^+$ complexes. The $Cu(NH_3)_2^+$ complex is weakly bound in the zeolite (Janssens, T. V. W. et al., ACS Catal. 5, 2832-2845 (2015); Paolucci, C.

et al., J. Am. Chem. Soc. 138, 6028-6048 (2016)), which suggests that this complex is mobile under reaction conditions for $NH_3$-SCR.

Applicant's patent applications WO 2015/154829 A1, WO 2015/154828 A1 and WO 2015/154827 A1 describe methods for the preparation of Cu-zeolite and Cu-zeotype materials by mixing a given zeolite or zeotype material in the $H^+$ or $NH_4^+$ form with CuO or $Cu_2O$ powder, followed by exposure to $NH_3$ or a mixture of $NH_3$ with nitrogen oxides at temperatures below 300° C. The materials prepared in this way show an activity for $NH_3$-SCR that is comparable to or exceeds the activity of materials prepared by conventional ion exchange procedures, which means that solid state ion exchange can take place between Cu oxides and zeolites at temperatures below 300° C. in the presence of ammonia. It has been proposed that the ability of performing ion-exchange at low temperatures is due to the mobility of the $Cu(NH_3)_2^+$ complex (Shwan, S. et al., ACS Catal. 5, 16-19 (2015)). The role of the mobility for the activation of oxygen in $NH_3$-SCR in Cu-zeolites has not been established yet.

The above-mentioned WO 2015/154829 A1 discloses that the efficiency of the solid state ion exchange process decreases at temperatures above 350° C. Following the idea that the solid state ion exchange process is due to the mobility of the $Cu(NH_3)_2^+$ complex, it can be deduced from this result that the $Cu(NH_3)_2^+$ complex is not thermally stable above 350° C. This then leads to a loss of the mobility of the Cu-complex.

The present invention is built on the observations that oxidation of methane at around 200° C. requires an activation of oxygen on a Cu-zeolite or Cu-zeotype, which probably involves more than one Cu-center, and that the presence of ammonia enhances the mobility of the Cu-centers in a Cu-zeolite or Cu-zeotype.

The present invention concerns a process for the oxidation of a lower alkane over a catalyst containing Cu and a zeolite or a zeotype material at a process temperature below 350° C., wherein the oxidation is conducted in the presence of ammonia in the feed gas. The presence of ammonia is essential to the oxidation of methane on Cu-zeolite or Cu-zeotype materials, even though it does not directly take part in the oxidation of methane, and it is not necessarily a part of the reaction product. It is also noted that the process of the invention implies activation of oxygen at temperatures below 350° C., and does not require the oxygen activation above 400° C. as described in Le, H. et al., *ACS Catal.* 7, 1403-1412 (2017) and Markovits, M. A. C. et al., *Top. Catal.* 59, 1554-1563 (2016).

A lower alkane is a C1-C5 alkane. The preferred lower alkane is methane.

A preferred reaction product is methanol.

A first embodiment of the invention is a process in which a gas mixture comprising oxygen, ammonia and a lower alkane is contacted with a Cu-zeolite material at a temperature below 350° C., resulting in an alkane concentration in the product stream that is lower than the concentration in the inlet stream.

Another embodiment of the invention is a process in which a gas mixture comprising oxygen, ammonia and a lower alkane is contacted with a Cu-zeotype material at a temperature below 350° C., resulting in an alkane concentration in the product stream that is lower than the concentration in the inlet stream.

Another embodiment of the invention is a process in which a gas mixture comprising water, ammonia and lower alkane is contacted with a Cu-zeolite material at a temperature below 350° C., resulting in an alkane concentration in the product stream that is lower than the concentration in the inlet stream.

Another embodiment of the invention is a process in which a gas mixture comprising water, ammonia and lower alkane is contacted with a Cu-zeotype material at a temperature below 350° C., resulting in an alkane concentration in the product stream that is lower than the concentration in the inlet stream.

A further embodiment of the invention is a catalyst containing a mixture of a zeolite or a zeotype in the $H^+$ or $NH_4^+$ form and an oxide of Cu.

Preferably the zeolite structure of the Cu-zeolite catalyst is one or more structures selected from the group consisting of AEI, AFX, CHA, KFI, ERI, GME, LTA, IMF, ITH, MEL, MFI, SZR, TUN, *BEA, BEC, FAU, FER, MOR and LEV. It is especially preferred that the Cu-zeolite catalyst is selected from the group consisting of Cu-CHA, Cu-MOR, Cu-MFI, Cu-BEA, Cu-ZSM-5 and Cu-FER.

According to the present invention, the process feed gas mixture comprises oxygen, ammonia and a lower alkane. Other gaseous compounds, such as nitrogen, water, noble gases and other hydrocarbons, can be present in the feed gas mixture as well.

An advantage of the present invention is that the process can be conducted continuously without any need of re-activation of the Cu-zeolite or Cu-zeotype material.

Another advantage of the present invention is that the process can be conducted isothermally at a process temperature between 150 and 350° C. A preferred embodiment of the invention is a process in which the oxidation is performed at a temperature of 250° C. or lower.

A further embodiment of the invention is that the catalyst for the process comprises a mixture of a metal-free zeolite or zeotype material and an oxide of Cu.

Another embodiment of the invention is a process in which a gas mixture comprising oxygen, ammonia and a lower alkane is contacted with a catalyst containing Cu and one or more zeolite or zeotype materials at a temperature below 350° C., in which the concentration of $NH_3$ is between 1 and 5000 ppmv.

Another embodiment of the invention is a process in which a gas mixture comprising oxygen, ammonia and a lower alkane is contacted with a catalyst containing Cu and one or more zeolite or zeotype materials at a temperature below 350° C., in which the concentration of oxygen is 10 vol % or lower.

Another embodiment of the invention is a process in which a gas mixture comprising water, ammonia and a lower alkane is contacted with a catalyst containing Cu and one or more zeolite or zeotype materials at a temperature below 350° C., in which the concentration of water is 10 vol % or lower.

The invention claimed is:

1. A process for the oxidation of a lower alkane over a catalyst containing Cu and one or more zeolite or zeotype materials, wherein the oxidation is conducted in the presence of ammonia in a feed gas at a process temperature below 350° C.

2. Process according to claim 1, wherein a zeolite or zeotype material is mixed with an oxide of Cu.

3. Process according to claim 1, in which the oxidation is performed in a continuous process.

4. Process according to claim 1, wherein the lower alkane is methane.

5. Process according to claim 1, wherein the reaction product is methanol.

6. Process according to claim 1, wherein the zeotype is a silico-alumino phosphate material.

7. Process according to claim 1, wherein the content of ammonia in the feed gas is between 1 and 5000 ppmv.

8. Process according to claim 1, wherein a content of oxygen in the feed gas is 10 vol % or lower.

9. Process according to claim 1, wherein a content of water in the feed gas is 10 vol % or lower.

10. Process according to claim 1, wherein the process temperature is 250° C. or lower.

11. Process according to claim 1, wherein one or more zeolite or zeotype materials in the catalyst have structures selected from the group consisting of AEI, AFX, CHA, KFI, ERI, GME, LTA, IMF, ITH, MEL, MFI, SZR, TUN, *BEA, BEC, FAU, FER, MOR and LEV.

12. Process according to claim 1 wherein the Cu-zeolite catalyst is selected from the group consisting of Cu-CHA, Cu-MOR, Cu-MFI, Cu-BEA, Cu-ZSM-5 and Cu-FER.

13. Process according to claim 11, wherein the Cu-based catalyst is Cu-CHA.

14. The process according to claim 1, wherein the one or more zeolite or zeotype materials do not require reactivation.

15. The process according to claim 3, wherein the one or more zeolite or zeotype materials do not require reactivation.

* * * * *